United States Patent [19]

Tung et al.

[11] 4,172,100

[45] Oct. 23, 1979

[54] 1,3-BIS[1-(4-METHYLPHENYL)ETHENYL]-BENZENE

[75] Inventors: Lu H. Tung; Grace Y. Lo; Douglas E. Beyer, all of Midland, Mich.

[73] Assignee: The Dow Chemical Company, Midland, Mich.

[21] Appl. No.: 931,787

[22] Filed: Aug. 7, 1978

Related U.S. Application Data

[62] Division of Ser. No. 840,889, Oct. 11, 1977.

[51] Int. Cl.$^2$ .............................................. C07C 15/16
[52] U.S. Cl. ....................................... 585/25; 585/320
[58] Field of Search .................................... 260/668 R

[56] References Cited

U.S. PATENT DOCUMENTS 4,067,917  1/1978  Sigwalt ................................ 526/173

*Primary Examiner*—Veronica O'Keefe

[57] ABSTRACT

Highly desirable organic liquid soluble multifunctional lithium containing initiators are prepared by reacting an organo lithium compound with an organic compound containing at least one group of the configuration 1,3-bis(1-phenylethenyl)benzene. Such initiators can be prepared in the absence of polar solvents and are very desirable for the polymerization of dienes such as butadiene to a desirable 1,4 configuration.

1 Claim, No Drawings

1,3-BIS[1-(4-METHYLPHENYL)ETHENYL]BENZENE

This is a division of application Ser. No. 840,889, filed Oct. 11, 1977.

In the polymerization of 1,3-butadiene and isoprene, for many applications, it is highly desirable to polymerize the monomer in such a manner that the amount of 1,4 addition in the polydiene chains is maximized. Desirable initiators of polymerization are often polyfunctional lithium compounds, that is, compounds having two or more lithium atoms as the polymerization initiating sites and are desirable in the preparation of block copolymers and diene polymers having functional end groups. Many of these multifunctional compounds, from a practical standpoint, fail to provide all that is desired in a polymerization initiator for vinyl group containing compounds such as 1,3-butadiene, isoprene and the like. Oftentimes, traces of polar compounds such as ethers are present. Polar compounds in general tend to increase the amount of 1,2 addition during the polymerization of butadiene or isoprene. Usually it is very desirable to polymerize the diene in a hydrocarbon solvent. For uniformity of the product and maximum control, as well as ease of handling, it is desirable that an initiator be soluble in the polymerization system rather than merely dispersible as a particulate material. Multifunctional lithium containing initiators and their preparation are well known in the art as is the use of such initiators in the polymerization of olefinically unsaturated hydrocarbon monomers. Such polymers and initiators are disclosed in the following U.S. Pat. Nos. 3,660,536; 3,663,634; 3,668,263; 3,684,780; 3,725,368; 3,734,973; 3,776,893; 3,776,964; 3,784,637; 3,787,510; and 3,954,894, the teachings of which are herewith incorporated by reference thereto. One particularly desirable initiator has the formula:

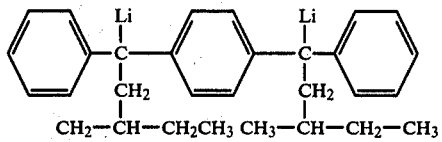

1,4-phenylenebis(3-methyl-1-phenylpentylidene)-bis(lithium)

Other useful initiators include those wherein the terminal phenyl groups have alkyl substitution. Such compounds are in general insoluble in hydrocarbon solvents usually employed for organo-lithium initiated polymerizations but can be solubilized by the addition of butadiene, isoprene or the like.

It would be desirable if there were available an improved hydrocarbon liquid soluble multifunctional lithium containing compound suitable for initiation of polymerization in a hydrocarbon medium.

It would also be desirable if an initiator was available which would promote polymerization of a 1,3-diene to give a high degree of 1,4 addition.

It would also be desirable if such an initiator were soluble in polymerization initiation quantities in a hydrocarbon medium and could be readily handled by pumping and the like.

These benefits and other advantages in accordance with the present invention are achieved in a multifunctional, lithium containing, polymerization initiating compound of the Formula:

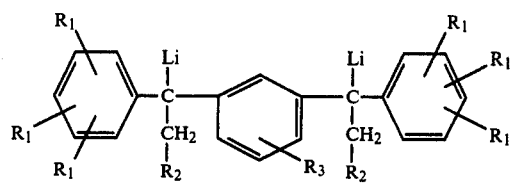

wherein $R_1$ and $R_3$ are individually selected from the group consisting of hydrogen, alkyl hydrocarbon radicals and alkoxy radicals, with the further limitation that $R_1$ and $R_3$ contain from 0 to 16 carbon atoms, $R_2$ is a hydrocarbyl radical. Preferably, the hydrocarbyl radical is a secondary butyl group.

Also contemplated within the scope of the present invention is a solution particularly suited for the initiation of polymerization of vinyl group containing compound which are polymerizable in the presence of a lithium containing initiator particularly vinyl hydrocarbon compounds, the solution comprising a major portion of a solvent selected from the group consisting of liquid aliphatic, cycloaliphatic and aromatic hydrocarbons and mixtures thereof and a minor proportion of a multifunctional lithium containing polymerization initiating compound of the formula:

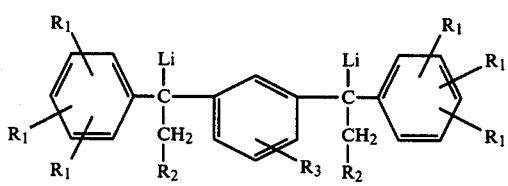

wherein $R_1$ and $R_3$ are individually selected from the group consisting of hydrogen, alkyl hydrocarbon radicals and alkoxy radicals, with the further limitation that $R_1$ and $R_3$ contain from 0 to 16 carbon atoms, and $R_2$ is a hydrocarbyl radical. Preferably, the hydrocarbyl is a secondary butyl group.

Also contemplated within the scope of the present invention is a method for the polymerization of vinyl compounds containing at least one vinyl group and particularly vinyl hydrocarbon compounds which are polymerizable in the presence of a lithium containing catalyst, the steps of the method comprising providing a solution of the reaction of the product of a compound of the formula:

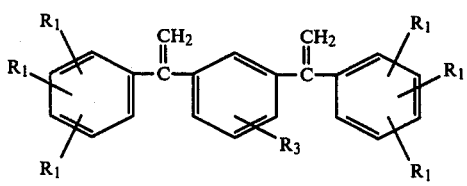

wherein $R_1$ and $R_3$ are individually selected from the group consisting of hydrogen, alkyl hydrocarbon radicals and alkoxy radicals, with the further limitation that $R_1$ and $R_3$ contain from 0 to 16 carbon atoms, and a lithium containing compound of the formula:

$R_2Li$ wherein $R_2$ is a hydrocarbyl radical to provide a multifunctional lithium compound having the formula:

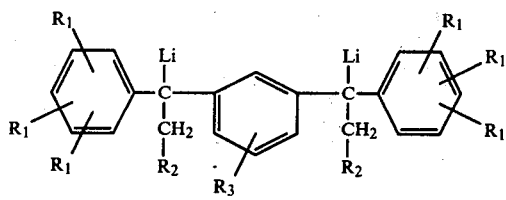

and subsequently contacting the resultant solution with at least one organolithium polymerizable monomer to cause the polymerization of the monomer to a corresponding polymer.

$R_1$ and $R_3$ in the foregoing formulas beneficially are individually selected from the group consisting of hydrogen, alkyl or alkoxy radicals such as methyl, ethyl, propyl, isopropyl, tertiary butyl, pentyl, hexyl, octyl, nonyl, decyl, dodecyl, tetradecyl, hexadecyl of straight chain configuration or any of the position isomers thereof. The corresponding alkoxyl radicals are also useful.

$R_2$ is a hydrocarbyl radical and includes methyl, ethyl, butyl, hexyl, dodecyl, eicosyl, and the like radicals as well as cycloalkyl and radicals such as cyclohexyl, cyclopentyl which may be substituted with alkyl, cycloalkyl or aromatic radicals. Aromatic radicals such as phenyl, benzyl, are also useful as $R_2$. Other radicals which are employed as $R_2$ include hydrocarbyl oligomers and polymers as well as co-oligomers and copolymers. Such hydrocarbyl radicals include: polybutadienyl, polystyryl, polyisoprenyl, radicals of co-oligomers of styrene and butadiene, styrene and isoprene, isoprene and butadiene, as well as terpolymer oligomers and polymers of such hydrocarbyl unsaturated monomers. When employing polymers to form the $R_2$ group, a compound such as Compound II serves as a coupling agent as the living polymers added to the ethylenic unsaturation and still provide two polymerization initiating sites which can be employed to initiate further polymerization and thus provide polymer molecules having four branches or arms.

Multifunctional initiators of the present invention are particularly useful for the preparation of thermoplastic elastomers and impact resistant thermoplastic resinous polymers of butadiene, isoprene or mixtures thereof and styrene. Beneficially, living polymers or polymers with reactive ends are also readily prepared. For example, the resultant lithium terminated or living polymers are reacted with sulfur, ethylene sulfide, propylene sulfide and the like to provide a thiol capped polymer which in turn may be used to prepare a block polymer using free radical polymerization using one or more monomers which may not be satisfactorily polymerized with lithium catalysts.

Exemplary compounds employed herein include:

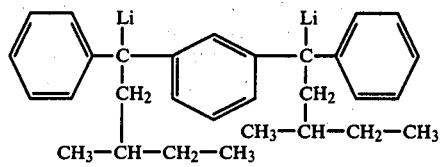

I.

1,3-phenylene-bis(3-methyl-1-phenylpentylidene)bis(lithium)

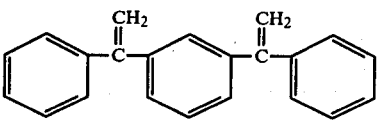

II 1,3-di(1-phenylethenyl)benzene

Compounds in accordance with the present invention are readily prepared from compounds of the type hereinbefore disclosed and are readily synthesized from a 1,3 disubstituted benzene. For example, one mole of 1,3-diacetylbenzene is reacted with an excess of phenyl magnesium bromide and the resulting compound dehydrated to Compound II. An alternate route to the same compound is one mole isophthaloyl dichloride with excess benzene in the presence of a Freidel-Crafts catalyst to provide a diketone which is reacted with an excess of methyl magnesium iodide and the product dehydrated to obtain Compound II. The foregoing procedures are readily employed to provide divinylidene compounds similar to Compound II but having the terminal phenyl group ring substituted. The divinylidene compound is then contacted with an organo lithium compound such as secondary butyllithium, tertiary butyllithium and the like. The organo lithium compound adds to the double bonds to provide the desired polymerization initiating compound. The resulting dilithium compound is soluble in both cycloaliphatic or aromatic hydrocarbon solvent such as cyclohexane, benzene, toluene or mixtures thereof and the like. If p-tolyl magnesium bromide is employed in place of phenyl magnesium bromide a compound is obtained having a single methyl group on each terminal benzene ring. Alternatively in the second mentioned method of preparation, excess toluene may be employed in place of excess benzene. Such compounds having alkyl substitution on the terminal rings are soluble in any one of aliphatic, cycloaliphatic or aromatic hydrocarbon solvents such as n-hexane, cyclohexane, benzene, toluene and the like or mixtures thereof.

EXAMPLE I

A Grignard reagent was prepared by admixing 0.4 mole of bromobenzene with 0.6 mole of magnesium turnings in 260 milliliters of diethyl ether. After the reaction was complete, the resultant solution was added over a period of twenty minutes to 0.1 mole of meta-diacetylbenzene dissolved in 500 milliliters of benzene. The resultant mixture was refluxed at atmospheric pressure for a period of two hours and the contents of the reaction vessel were then poured into ice water. After agitation, in separatory funnel, the water and organic layer were separated, the aqueous layer discarded, the organic layer washed with water and then with a saturated aqueous solution of sodium chloride. The remaining organic layer was dried with anhydrous magnesium sulfate and the dried organic layer was evaporated in a rotary evaporator providing 1,3-di(1-phenyl-1-hydroxyethyl)benzene. The product was then dissolved in 500 milliliters of benzene which contained 0.25 gram of toluene sulfonic acid monohydrate. The benzene solution was then refluxed for a period of two and one-half hours using a Dean Stark assembly. When refluxing was completed, the mixture was cooled, washed with water, aqueous sodium bicarbonate and a third wash with saturated aqueous sodium chloride solution. The organic layer was then dried with anhydrous magnesium sulfate and the benzene was then removed employing a rotary evaporator. The residue was brown oil which was distilled under a pressure of about 0.1 millimeter of mercury. The fraction boiling from about 154° C. to 160° C. was a supercooled viscous yellow oil. Infrared and nuclear magnetic resonance spectroscopy were employed to confirm that the product was 1,3-di(1-phenylethenyl)benzene (Compound II). The oil was a supercooled liquid and can be used directly in the preparation of a dilithium initiator as set forth in the following description or crystallized before use. A portion of the oil was dissolved in warm ethanol in a glass container, the resulting ethanol solution cooled to about $-20°$ C. and the inner wall of the breaker rubbed with a glass stirring rod to initiate crystallization. Later crystallizations employed seeding. The crystals are colorless, needlelike and melt over the range 45.5° to 46.5° C. A solution was prepared of 0.96 millimole of Compound II in a 20 milliliters of toluene contained in a nitrogen-filled flask equipped with a magnetic stirrer and a rubber septum capped side arm. To this mixture were added 2.03 millimoles of secondary butyllithium in cyclohexane. The reaction mixture turned redish-brown in color and the temperature was maintained between about 28° and 30° C. No precipitate was observed at any time. The reaction mixture was sampled periodically after the addition of the secondary butyllithium by withdrawing 4 milliliter aliquots. The aliquots were withdrawn at 10 minutes, 30 minutes, 60 minutes, 90 minutes and 180 minutes after the addition of the secondary butyllithium. Each of the aliquots were mixed with 0.1 milliliter of glacial acetic acid. The aliquots were then centrifuged to remove lithium acetate. After removal of the lithium acetate, most of the solvent was removed by evaporation. The remaining products were then analyzed by gel permeation chromatography which showed the complete transformation of Compound II to 1,3-phenylene-bis-(3-methyl-1-phenylpentylidene)bis-(lithium) within 30 minutes.

Polymerization was conducted in the following manner: 1.53 millimoles of secondary butyllithium was added to a small nitrogen-filled flask containing 0.75 millimole of Compound II dissolved in 17 milliliters of toluene. The reaction mixture was maintained within the temperature range of 27° C. to 30° C. At the end of 35 minutes after the addition of the secondary butyllithium, the contents of the flask were dark red, slightly viscous solutions of Compound I. A one-liter flask was charged with 47 grams of butadiene dissolved in 400 milliliters of toluene. The butadiene toluene solution was treated with 0.3 millimole of secondary butyllithium to remove moisture, oxygen, and other impurities which would interfere with an organolithium-initiated polymerization. The toluene solution of the Compound I was added to the one liter flask by means of a syringe. The one liter flask was placed in a water bath having a temperature of from about 50° to 60° C. Polymerization of the butadiene appeared to be complete after about 70 minutes. At this time, 25.4 grams of styrene and 2 milliliters of tetrahydrofuran were added. The reaction mixture immediately assumed the characteristic coloration of an organolithium-induced styrene polymerization. The water bath was removed and polymerization was complete about 50 minutes after the addition of the styrene. Four milliliters of methanol were added and the resultant polymer recovered by precipitation in methanol. The molecular weight of the polymer was determined employing gel permeation chromatography. The molecular weight was 112,000 (weight average). The polymer was analyzed and found to contain 33 percent by weight styrene. A portion of the resultant triblock copolymer was molded and had a tensile strength at rupture of 3400 lb./sq. inch and elongation at break of about 950 percent. It is believed that such properties clearly indicate that the polymer is essentially a triblock with little or no contamination by diblock or homopolymers.

A tapered or graded styrene-butadiene-styrene block copolymer (such polymers are described in U.S. Pat. No. 3,906,058 herewith incorporated by reference thereto) was prepared in the following manner: A nitrogen purged flask was used to prepare a solution of 0.729 millimoles of Compound II in toluene. A solution of 1.394 millimoles of secondary butyllithium dissolved in cyclohexane was added and the mixture permitted to stand at room temperature for a period of two and one-half hours. The resultant solution was a solution of the dilithium initiator Compound I. At this time the initiator solution was added to a nitrogen-purged one-liter flask containing 450 milliliters of toluene, 34 grams of butadiene and 30 grams of styrene. The toluene-butadiene-styrene solution had been de-aired and impurities removed with 0.29 millimoles of secondary butyllithium. The one-liter flask and contents were placed in a water bath, maintained at a temperature of 50° to 55° C. After remaining in the water bath for 110 minutes, one milliliter of methanol was added to terminate any anions present. The contents of the one-liter flask were poured into methanol and a precipitate formed. On drying, the precipitate weighed 63 grams and was rubbery in nature. The product was a graded block copolymer of styrene-butadiene-styrene containing about 48 weight percent styrene. The block copolymer had a molecular weight of 144,000 (weight average) as determined by gel permeation chromatography. A portion of the polymer was compression molded. Compression molded samples had a tensile strength at rupture of 3,400 pounds per square inch and an ultimate elongation of 800 percent.

EXAMPLE 2

A reaction vessel was charged with 144.5 grams of aluminum chloride, 300 milliliters of toluene. A solution of 100.1 grams of isophthaloyol dichloride dissolved in 150 milliliters of toluene was added over a one hour period while the vessel and contents were maintained at a temperature below about 40° C. The reaction mixture was stirred for 30 minutes after completion of the addition of the dichloride-toluene solution. The reactor and contents were then heated to 90° C. over a period of 30 minutes and maintained at that temperature for an additional 60 minutes. The flask and contents were then cooled at ambient temperature for an additional 30 minutes. At the end of this period, the mixture was poured over one kilogram of ice, and chloroform was added to the reaction mixture to dissolve solids which formed on cooling. A water layer and an organic layer were present when the ice had melted. The organic layer was separated and washed with one liter of water. The aqueous layer and the water wash from the organic layer were combined and the combination was extracted twice with 100 milliliter portions of chloroform and the chloroform extract combined with the organic layer and washed with one liter of saturated aqueous sodium chloride. The organic layer was separated and dried over anhydrous magnesium sulfate. The organic layer was filtered to remove the magnesium sulfate and solvent removed from the organic layer in a rotary evaporator to yield solid 1,3-di(4-methylbenzoyl)benzene which was recrystallized twice from absolute ethanol. A Grignard reagent solution was prepared in the following manner: 118 milliliters of a 1 to 1 by volume mixture of iodomethane and diethyl ether were added to 23.2 grams of magnesium turnings in 150 milliliters of diethyl ether. The mixture was stirred for one hour. A solution was prepared of 50 grams of 1,3-di(4-methylbenzoyl)benzene in 500 milliliters of toluene. The Grignard reagent solution was added to the 500 milliliter toluene solution over a period of ¼ hour. The resultant mixture was refluxed for one and one-half hours and allowed to stand and cool to room temperature. The cooled mixture was then poured over one kilogram of ice. When the ice had melted, the aqueous layer was acidified with a 15 percent aqueous hydrochloric acid solution to dissolve solids present and the aqueous and organic layers separated. The aqueous solution was extracted twice with 100 milliliter portions of toluene. The toluene was combined with the organic layer and the resultant organic phase was washed with 500 milliliters of saturated aqueous sodium chloride. The organic phase was then separated and dried with anhydrous magnesium sulfate to provide a solution of 1,3-di[1-(4-methylphenyl)1-hydroxyethyl]benzene in toluene. The solution of 1,3-di[1-(4-methylphenyl)1-hydroxyethyl]benzene was mixed with 0.25 gram of toluene sulfonic acid monohydrate and the solution refluxed for 45 minutes in a Dean-Stark assembly. After 200 milliliters of solvent had distilled, the mixture was maintained under total reflux for an additional 45 minutes. The reaction mixture was then washed once with 500 milliliters of aqueous sodium bicarbonate, once with 500 milliliters of water and once with 500 milliliters of saturated aqueous sodium chloride. The organic phase was separated from the sodium chloride solution and dried over anhydrous magnesium sulfate. The organic phase was filtered and the solvent removed in a rotary evaporator to leave a yellow oil which solidified on standing. The reaction product was purified by twice recrystallizing from absolute ethanol to provide a white crystalline solid 1,3-di[1-(4-methylphenyl)ethyl]benzene.

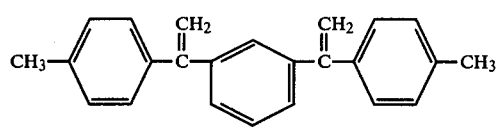

The melting point range was 65° to 66° C. The material distills at 177° C. at about 0.13 millimeter of mercury. A nitrogen-purged flask was provided which contained 15 milliliters of toluene having 0.668 millimole of 1,3-di[1-(4-methylphenyl)ethenyl]benzene. A solution of 1.340 milliequivalents of secondary butyllithium in cyclohexane was added to the toluene solution. After three hours at room temperature, the diethenyl compound was converted to 1,3-phenylene-bis(3-methyl-1,[4-methylphenyl]pentylidene)bis(lithium).

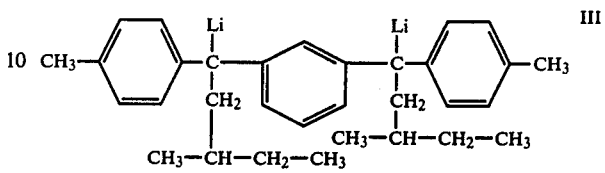

The compound is soluble in normal hexane and can be prepared in normal hexane instead of toluene. A 1-liter nitrogen filled reaction flask had charged therein 39 grams of butadiene dissolved in 450 milliliters of toluene which had previously been treated with 0.275 milliequivalents of secondary butyllithium to destroy active impurities therein. The toluene solution of the dilithium initiator was added to the 1-liter reaction flask and the flask heated with a water bath maintained at about 50° C. After a period of about 80 minutes, the polymerization of the butadiene was for practical purposes complete. At this time, two milliliters of distilled tetrahydrofuran and 23 milliliters of purified styrene monomer were added. Polymerization of styrene continued for a period of about 40 minutes without heating. At the end of this period, one milliliter of methanol was added to the reaction mixture to terminate or kill any anions present. The reaction mixture was recovered by precipitation in methanol. When dried, the polymer weighed 65 grams and had a molecular weight as determined by gel permeation chromatography of 114,000. A portion of the polymer was molded and determined to have a tensile strength at break of 3160 pounds per square inch and an elongation of 790 percent.

EXAMPLE 3

The procedure of Example 1 is repeated with the exception that 1-bromo-4-tertiarybutylbenzene is employed in place of bromobenzene. 1,3-Phenylene-bis-[3-methyl-1,(4-tertiarybutylphenyl)pentylidene]-bis(lithium) IV is obtained.

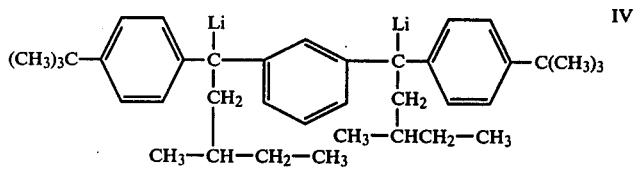

The compound will have the properties generally commensurate with the properties of Compound I prepared in the illustration.

EXAMPLE 4

The procedure of Example 1 is repeated with the exception that 1-bromo-4-ethylbenzene is employed in place of bromobenzene. 1,3-Phenylene-bis-[3-methyl-1(4-ethylphenyl)pentylidene]bis(lithium) (V) is obtained.

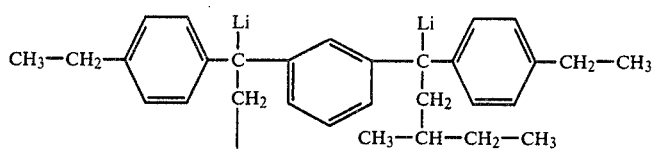

The compound will have the properties generally commensurate with the properties of Compound I prepared in the illustration.

EXAMPLE 5

The procedure of Example 1 is repeated with the exception that 1,2-dimethyl-4-bromobenzene is employed in place of bromobenzene. 1,3-Phenylene-bis-[3-methyl-1(3,4-dimethylphenyl)pentylidene]bis(lithium) VI is obtained.

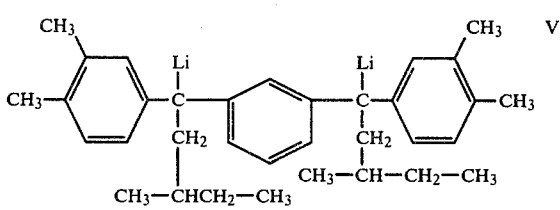

The compound will have the properties generally commensurate with the properties of Compound I prepared in the illustration.

EXAMPLE 6

The procedure of Example 1 is repeated with the exception that normal butyllithium is employed in place of secondary butyllithium. 1,3-Phenylene-bis-(1-phenyl-hexylidene)bis(lithium) VII is obtained.

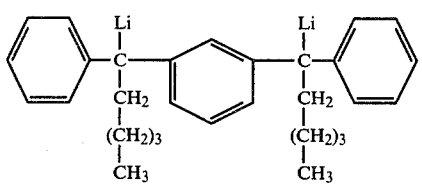

The compound will have the properties generally commensurate with the properties of Compound I prepared in the illustration

EXAMPLE 7

The procedure of Example 1 is repeated with the exception that isopropyllithium is employed in place of secondary butyllithium. 1,3-Phenylene-bis-[3-methyl-1-phenylbutylidene]bis(lithium) VIII is obtained.

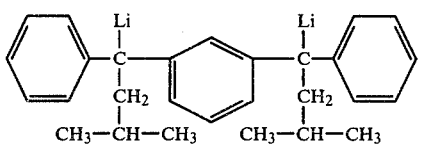

The compound will have the properties generally commensurate with the properties of Compound I prepared in the illustration.

EXAMPLE 8

The procedure of Example 1 is repeated with the exception that n-propyllithium is employed in place of secondary butyllithium. 1,3-Phenylene-bis(1-phenylpentylidene)bis(lithium) IX is obtained.

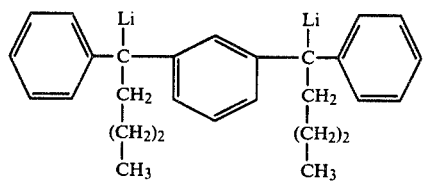

The compound will have the properties generally commensurate with the properties of Compound I prepared in the illustration.

EXAMPLE 9

One-hundred eight grams of uvitic acid are admixed with 500 grams of thionyl chloride and 2 milliliters of pyridine. The resultant mixture was refluxed at atmospheric pressure for a period of 12 hours. On completion of reflux, thionyl chloride is removed by distillation under vacuum on a steam bath. The residue is then vacuum distilled under a pressure of about 0.5 millimeter of mercury to provide uvitic acid chloride. When the uvitic acid chloride is employed in the preparative procedure of Example 2 in place of isophthaloyl dichloride, the resultant product is 1,3-(5-methylphenylene)-bis(3-methyl-1-[4-methylphenyl]pentylidene)bis(lithium).

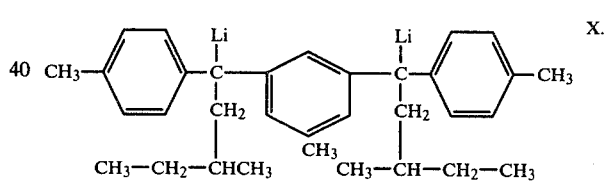

The compound will have properties generally commensurate with Compound I prepared in the illustration. No support for alkoxy radical.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. 1,3-bis[1-(4-methylphenyl)ethenyl]benzene having the formula:

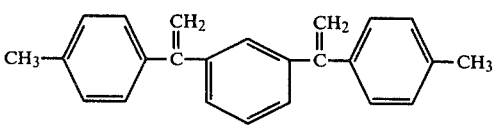

* * * * *